US008476477B2

(12) United States Patent
Yu et al.

(10) Patent No.: US 8,476,477 B2

(45) Date of Patent: Jul. 2, 2013

(54) PROCESS OF OXIDATIVE CONVERSION OF METHANOL

(75) Inventors: Peng Yu, Beijing (CN); Jingsong Liu, Beijing (CN); Junfeng Rong, Beijing (CN); Changzhi Shi, Beijing (CN); Qiang Fu, Beijing (CN); Jin Wang, Beijing (CN); Wei Zhang, Beijing (CN); Xuhua Zhou, Beijing (CN)

(73) Assignees: China Petroleum & Chemical Corp., Beijing (CN); Research Institute of Petroleum Processing, Sinopec, Beijing (CN)

( * ) Notice: Subject to any disclaimer, the term of this patent is extended or adjusted under 35 U.S.C. 154(b) by 517 days.

(21) Appl. No.: 12/713,552

(22) Filed: Feb. 26, 2010

(65) Prior Publication Data

US 2011/0054221 A1 Mar. 3, 2011

(30) Foreign Application Priority Data

Feb. 27, 2009 (CN) .......................... 2009 1 0078391

(51) Int. Cl.
*C07C 41/50* (2006.01)
*C07C 43/315* (2006.01)

(52) U.S. Cl.
CPC ............... *C07C 41/50* (2013.01); *C07C 43/315* (2013.01)
USPC .......................................... 568/594; 568/601

(58) Field of Classification Search
USPC ................................................ 568/594, 601
See application file for complete search history.

(56) References Cited

U.S. PATENT DOCUMENTS

| | | | | |
|---|---|---|---|---|
| 5,959,156 | A | 9/1999 | Hagen et al. | |
| 6,166,266 | A | 12/2000 | Hagen et al. | |
| 6,350,919 | B1 | 2/2002 | Hagen et al. | |
| 6,392,102 | B1 | 5/2002 | Hagen et al. | |
| 6,534,685 | B1 | 3/2003 | Patrini et al. | |
| 6,737,545 | B1 * | 5/2004 | Hibst et al. | 562/535 |
| 7,560,599 | B2 | 7/2009 | Chen et al. | |
| 7,671,240 | B2 | 3/2010 | Stroefer et al. | |
| 7,759,525 | B2 * | 7/2010 | Dubois et al. | 568/593 |
| 2005/0154226 | A1 | 7/2005 | Liu et al. | |

FOREIGN PATENT DOCUMENTS

| | | | |
|---|---|---|---|
| CN | 1034680 | A | 8/1989 |
| CN | 1005387 | B | 10/1989 |
| CN | 1187462 | A | 7/1998 |
| CN | 1205915 | A | 1/1999 |
| CN | 1069553 | C | 8/2001 |
| CN | 1111086 | C | 6/2003 |
| CN | 1121979 | C | 9/2003 |
| CN | 1257840 | C | 5/2006 |
| CN | 101054339 | A | 10/2007 |
| CN | 101182367 | A | 5/2008 |
| CN | 101199939 | A | 6/2008 |
| CN | 101224431 | A * | 7/2008 |
| DE | 10 2005 02770 | | 12/2006 |
| EP | 1505049 | A1 | 2/2005 |
| JP | 63022536 | A | 1/1988 |
| WO | WO 00/29364 | | 5/2000 |

OTHER PUBLICATIONS

Li et al., "A study of methanol oxidation to formaldehyde on Fe—Mo/KZSM-5 zeolite, Chinese Journal of Catalysis," vol. 20 No. 4, Jul. 1999.
Search report for EP10 00 2007 dated Aug. 2, 2010.
English abstract of CN 1187462 A, Jul. 1998.
English abstract of CN 1121979 C, Sep. 2003.
English abstract of CN 1257840 C, May 2006.
English abstract of CN 1069553 C, Aug. 2001.
English abstract of CN 1205915 A, Jan. 1999.
English abstract of JP 63022536 A, Jan. 1998.
English abstract of CN 101054339 A, Oct. 2007.
English abstract of CN 101199939 A, Jun. 2008.
English abstract of CN 101182367 A, May 2008.
English abstract of CN 1111086 C, Jun. 2003.
English abstract of DE 10 2005 027701 A1, Dec. 2006.
English abstract of CN 1034680 A, Aug. 1989.

* cited by examiner

*Primary Examiner* — Rosalynd Keys
(74) *Attorney, Agent, or Firm* — Finnegan, Henderson, Farabow, Garrett & Dunner, LLP

(57) ABSTRACT

A process for preparing polyoxymethylene dimethyl ethers from methanol is disclosed. For example, the process comprises contacting methanol with at least one oxidant in the presence of at least one catalyst wherein the at least one catalyst comprises at least one Group VIB metal component, such as in an amount of from about 0.5 to about 50 wt % (in terms of metal oxide) and at least one Group VIII metal component, such as in an amount of from about 0.2 to about 20 wt % (in terms of metal oxide), and at least one molecular sieve having acidic catalytic activity, such as in an amount of from about 40 to about 95 wt %, based on the total weight of the at least one catalyst for a time sufficient to obtain polyoxymethylene dimethyl ethers.

31 Claims, 2 Drawing Sheets

PROCESS OF OXIDATIVE CONVERSION OF METHANOL

This application claims the benefit of priority under 35 U.S.C. §119 to Chinese Application No. CN200910078391.8, filed on Feb. 27, 2009.

Disclosed herein is a process of conversion of methanol, such as a process of converting methanol to polyoxymethylene dimethyl ethers ("DMMx").

An aspect in the research of C1 technology is to produce various useful chemicals from methanol.

For example, dehydration of methanol in the presence of a catalyst can result in dimethyl ethers, having good combustion characteristics related to high hexadecane numbers. Dimethyl ethers can be widely used as substitutes for liquid petroleum gas and vehicle fuels, e.g., for civil use. In addition, dimethyl ethers can be used as propellants for aerosol, foaming agents, solvents and extractants, etc.

In making polyoxymethylene dimethyl ethers ($CH_3O(CH_2O)_xCH_3$, $DMM_x$, $2 \leqq x \leqq 8$), borosilicates exhibiting the MFI crystal structure or an ion-exchange resin having proton acids can be used as catalysts. Furthermore, in making polyoxymethylene dimethyl ethers ($CH_3O(CH_2O)_xCH_3$, $DMM_X$, $2 \leqq x \leqq 5$), fluorosulfonic acid can be used as a catalyst.

Polyoxymethylene dimethyl ethers ($DMM_X$) with a hexadecane number of larger than 60 can be used as engine fuels in compression ignition internal combustion diesel engines or as additives for diesel fuels. Furthermore, since polyoxymethylene dimethyl ethers exist as liquids at ambient temperatures, they can be easily stored and transported.

An aspect of the disclosure involves oxidative conversions of methanol to polyoxymethylene dimethyl ethers, comprising contacting methanol with at least one oxidant in the presence of at least one catalyst, wherein the at least one catalyst comprises at least one Group VIB metal component, at least one Group VIII metal component, and at least one molecular sieve having acidic catalytic activity for a time sufficient to prepare polyoxymethylene dimethyl ethers.

A "metal component" as used herein refers to any compound or complex that comprises at least one metal. For example, a metal component can be salt(s), oxide(s), or sulfide(s). For a further example, a metal component is oxide(s).

In one embodiment, the at least one Group VIB metal component is present in the at least one catalyst in an amount of from about 0.5 to about 50 wt % (in terms of metal oxide), the at least one Group VIII metal component is present in an amount of from about 0.2 to about 20 wt % (in terms of metal oxide), and the at least one molecular sieve having acidic catalytic activity is present in an amount of from about 40 to about 95 wt %, based on the total weight of the at least one catalyst.

Further disclosed herein is a gas-phase process of preparing polyoxymethylene dimethyl ethers (DMMx) from methanol, comprising mixing methanol and at least one oxidant to form a binary mixed gas of the methanol and the at least one oxidant, feeding the mixed gas into a reactor, passing the mixed gas through a catalyst bed to form a product mixture containing DMMx, and adjusting the temperature of the reactor under controlled thermal condition. A catalyst bed comprises at least one catalyst. An aspect of the process disclosed herein is the conversion of methanol to dimethyl ether and polyoxymethylene dimethyl ethers ($DMM_X$, $2 \leqq x \leqq 8$) in one step.

Figure 1:
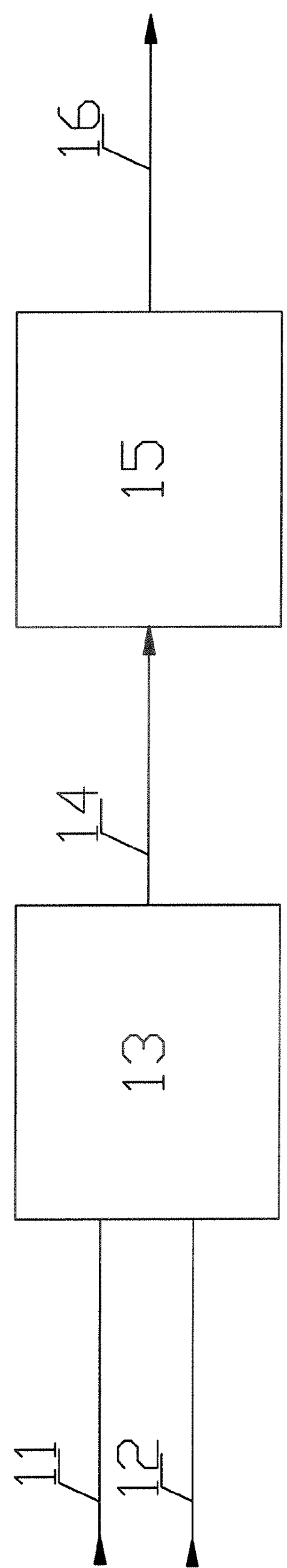
FIG. 1 is a representative schematic view of a process of preparing polyoxymethylene dimethyl ethers from methanol in one step according to one embodiment disclosed herein.

It is noted that, as used in the specification and the appended claims, the singular forms "a", "an" and "the" include plural referents (plural referents are also included in the phrase "at least one," the phrase covering plural instances when there is more than one of the referents, as well as singular instances where there is just one of the referents) unless the context clearly dictates otherwise.

According to an aspect of the process disclosed herein, the at least one Group VIB metal component in the at least one catalyst comprises molybdenum, and/or the at least one Group VIII metal component in the at least one catalyst comprises iron. For example, the amount of the at least one Group VIB metal component (in terms of metal oxide) can range from about 2 to about 20 wt %, and, as a further example, the amount of the at least one Group VIII metal component (in terms of metal oxide) can range from about 0.2 to about 10 wt % based on the total weight of the at least one catalyst.

For example, the at least one molecular sieve having acidic catalytic activity can be chosen from mesoporous molecular sieves, i.e., molecular sieves having mesoporous structures, and macroporous molecular sieves, i.e., molecular sieves having macroporous structures. As a further example, the mesoporous molecular sieves can be chosen from ZSM-5 molecular sieves, and/or the macroporous molecular sieves can be chosen from Y-type molecular sieves. As an even further example, the mesoporous molecular sieves can be chosen from ZSM-5 molecular sieves having a ratio of $SiO_2/Al_2O_3 \geqq 50$, and/or the macroporous molecular sieves can be chosen from Y-type molecular sieves including HY, REY, REHY, USY, and REUSY. As yet a further example, the Y-type molecular sieves can be chosen from HY, REY, REHY, USY, and REUSY. As yet an even further example, the Y-type molecular sieves can be chosen from REY and REHY. For example, the amount of the molecular sieves can range from about 60 to about 90 wt %, such as from about 70 to about 90 wt %, based on the total weight of the at least one catalyst.

The at least one molecular sieve can be commercially available or can be prepared by any known methods in the art. For example, phosphor- or rare earth elements-containing ZSM-5 molecular sieves having different silica alumina ratios and crystal grains can be prepared by known methods. HY, REY, REHY, USY and REUSY molecular sieves can also be prepared by known methods. A single molecular sieve or a combination of sieves can be used. For example, at least one intergrowth molecular sieve having acidic catalytic activity can be used.

There are no particular limitations on processes for preparing the at least one catalyst as long as the conditions are sufficient to load the metal components onto the molecular sieve. For example, one method for preparing the at least one catalyst comprises: preparing an aqueous solution of an appropriate metal component, then impregnating an appropriate molecular sieve having acidic catalytic activity with the solution, and drying and optionally calcinating the molecular sieve.

The methods and conditions for drying and optionally calcinating are well-known for preparing catalysts. For example, drying can be conducted at a temperature ranging from about 50 to about 300° C. for a period ranging from about 0.5 to about 12 hours, and as a further example, at a temperature ranging from about 100 to about 250° C. for a period ranging from about 1 to about 6 hours. Calcination can be, for example, conducted at a temperature ranging from about 350 to about 650° C. for a period ranging from about 0.5 to about 12 hours, and as a further example, at a temperature ranging from about 400 to about 600° C. for a period ranging from about 1 to about 4 hours.

In the processes disclosed herein, the at least one catalyst can be any molded product in a form chosen, for example, from microspheres, spheres, tablets, and strips. Molding can be conducted by conventional methods chosen, for example, from tablet molding, extruding molding, and rolling sphere molding. Molding can be operated either by molding the molecular sieve followed by loading the molecular sieve with metal components or by mixing the molecular sieve with the metal components followed by molding the mixture, as long as the at least one catalyst can be easily molded.

When using conventional methods for molding a catalyst, it is permissible to introduce adjuvants into a mixture that is to be molded to ensure smooth molding operation. For example, when molding strips by extrusion, suitable amounts of extrusion aids and water can be introduced into the mixture before the extrusion. The categories and amounts of the extrusion aids used can be conventional in the art. For example, typical extrusion aids can be chosen from sesbania powder, methyl cellulose, starch, polyvinyl alcohol, and a combination thereof.

In a process disclosed herein, the at least one catalyst can further comprise at least one heat-resistant inorganic oxide matrix. For example, the amount of the at least one heat-resistant inorganic oxide matrix is present in an amount of no more than 80 wt %, such as no more than 60 wt % of the total weight of the at least one catalyst.

The at least one heat-resistant inorganic oxide matrix disclosed herein may be chosen from heat-resistant inorganic oxides, which are usually used as matrices for catalysts. For example, the heat-resistant inorganic oxides are chosen from alumina, silica (silicon oxide), titanium oxide, magnesium oxide, silica-alumina, silica-magnesium oxide, silica-zirconium oxide, silica-thorium oxide, silica-beryllium oxide, silica-titanium oxide, silica-zirconium oxide, titanium oxide-zirconium oxide, silica-alumina-thorium oxide, silica-alumina-titanium oxide, silica-alumina-magnesium oxide, and silica-alumina-zirconium oxide. As a further example, the heat-resistant inorganic oxides are chosen from alumina, silica, and silica-alumina.

When the at least one catalyst comprises at least one heat-resistant inorganic oxide matrix, there is no particular limitation on the preparation method of the at least one catalyst provided that the conditions are sufficient for loading the metal components into the mixture of the at least one molecular sieve and the at least one heat-resistant inorganic oxide matrix.

A representative method for preparing a catalyst comprises: (1) mixing a molecular sieve with a heat-resistant inorganic oxide matrix and/or a precursor thereof; (2) formulating an aqueous solution of compounds containing appropriate respective metal components; (3) impregnating the mixture of (1) with the solution of (2), followed by drying and optionally calcinating the mixture.

The drying and calcinating methods and conditions thereof are commonly known in the art. For example, drying is performed at a temperature ranging from about 50 to about 300° C. for a period ranging from about 0.5 to about 12 hours, and as a further example, at a temperature ranging from about 10 to about 200° C. for a period ranging from about 1 to about 6 hours. Exemplary conditions of calcination are temperatures ranging from about 350 to about 600° C. for a period ranging from about 0.5 to about 8 hours, and as a further example, temperatures ranging from about 400 to about 500° C. for a period ranging from about 1 to about 4 hours.

For example, when the at least one catalyst is prepared by mixing a precursor of a heat-resistant oxide matrix and a molecular sieve, a calcinating step can be included after the mixing step. The methods for calcination and the conditions thereof are those typically used in the preparation of catalysts. For example, drying, when used, is conducted at a temperature ranging from about 50 to about 300° C. for a period ranging from about 0.5 to about 12 hours, and as a further example, at a temperature ranging from about 10 to about 200° C. for a period ranging from about 1 to about 6 hours. Exemplary calcinating conditions utilize a temperature ranging from about 350 to about 600° C. for a period ranging from about 0.5 to about 8 hours, and as a further example, a temperature ranging from about 400 to about 500° C. for a period ranging from about 1 to about 4 hours.

According to a process disclosed herein, the at least one oxidant can be chosen from oxygen, air, and a gas mixture of air and/or oxygen with at least one additional gas, which is inert to methanol during the process. The at least one additional gas inert to methanol can be chosen, for example, from nitrogen and other gases inert to methanol. The oxygen content of the gas mixture can be, for example, ranging from about 1 to about 30% by volume.

As disclosed herein, there is no particular limitation on the reactor provided that the methanol and the at least one oxidant are sufficiently reacted, such as contact-reacted under the above conditions. For example, the reactor can be chosen from batch tank reactors, fixed-bed reactors, and fluidized-bed reactors. For example, the conditions for the reaction, such as contact-reaction, can be as follows: a reaction temperature ranging from about 50 to about 500° C., such as from about 100 to about 400° C., further such as from about 100 to about 300° C., and even further such as from about 200 to about 300° C., a reaction pressure ranging from about 0.1 MPa to about 5 MPa, such as from about 0.1 MPa to about 5 MPa, further such as from about 0.1 MPa to about 2 MPa, a mass space velocity of methanol feed ranging from about 0.5 to about 50 $h^{-1}$, such as from about 3 to about 30 $h^{-1}$, further such as from about 8 to about 20 $h^{-1}$, and the amount of the at least one oxidant is adjusted so that the molar ratio of oxygen to methanol in the contact-reaction ranges from about 0.01:1 to about 0.5:1, such as from about 0.05:1 to about 0.3:1.

Also disclosed herein, for example, is a gas-phase process of preparing polyoxymethylene dimethyl ethers (DMMx) from methanol, comprising mixing methanol and at least one oxidant to form a binary mixed gas of the methanol and the at least one oxidant, feeding the mixed gas into a reactor, passing the mixed gas through a catalyst bed to form a product mixture containing DMMx, and adjusting the temperature of the reactor under controlled thermal conditions.

For example, adjusting the temperature of the reactor under controlled thermal conditions may be accomplished by varying the mass space velocity of methanol feed. As a further example, adjusting the temperature of the reactor under controlled thermal conditions may also be accomplished by cooling with a cooling medium outside the catalyst bed, wherein the cooling medium is chosen, for example, from air, water, and heat transfer oil. As yet a further example, adjusting the temperature of the reactor under controlled thermal conditions may be accomplished by controlling a cycled amount of non-DMMx parts in the product mixture. For the purpose of adjusting the temperature of the reactor, all or some of the non-DMMX parts in the product mixture may be cycled. For example, controlling the cycled amount of non-DMMx parts in the product mixture may include partly or completely incorporating non-DMMx parts in the product mixture into the catalyst bed directly from the top of the reactor or from multi-points at separate stages, and controlling the temperature of the cycled non-DMMx parts to be from about 0° C. to about 150° C. The ratio of the amount of the cycled non-DMMx parts to the starting amount of methanol can, for example, be from 0.1:1 to about 100:1. And as a further example, any combination of the above procedures may be used.

For example, the at least one oxidant can be chosen from oxygen, air and a gas mixture of air and/or oxygen with at least one additional gas, which is inert to methanol during the process disclosed herein. The at least one additional gas, which is inert to methanol, is, for example, chosen from nitrogen and other inert gases inert to methanol. The oxygen content of the gas mixture can be, for example, from about 1 to about 30% by volume, when the oxidant is a gas mixture of oxygen and other gases which are inert to methanol in conditions as exemplarily disclosed herein.

There is no particular limitation on the reactor provided that the methanol and the oxygen containing gases are sufficiently reacted, such as contact-reacted, under conditions exemplarily disclosed herein. For example, the reactors can be chosen from batch tank reactors, fixed-bed reactors, and fluidized-bed reactors. Representative conditions for a reaction, such as a contact-reaction, are as follows: a reaction temperature ranging from about 50 to about 500° C., such as from about 100 to about 400° C., and further such as from about 100 to about 300° C., and even further such as from about 200 to about 300° C., a reaction pressure ranging from about 0.1 MPa to about 10 MPa, such as from about 0.1 MPa to about 5 MPa, further such as from about 0.1 MPa to about 2 MPa, a mass space velocity of methanol feed ranging from about 0.5 to about 50 $h^{-1}$, such as from about 3 to about 30 $h^{-1}$, further such as from about 8 to about 20 $h^{-1}$, and the amount of the at least one oxidant is adjusted so that the molar ratio of oxygen to methanol in the contact-reaction ranges from about 0.01:1 to about 0.5:1, such as from about 0.05:1 to about 0.3:1. For example, the catalyst bed can be a fixed bed, and the at least one catalyst can comprise at least one Group VIB metal component, at least one Group VIII metal component, and at least one molecular sieve having acidic catalytic activity.

The product mixture containing DMMx, for example, may optionally be fed into a separation stage. As disclosed herein, the product mixture can comprise dimethyl ethers, polyoxymethylene dimethyl ethers and water. The separation stage can comprise, for example, one or more operational units of flash evaporation, atmospheric distillation, and vacuum distillation to achieve a desired separation.

Referring to FIG. 1, further description is made about an exemplary process disclosed herein. Purified methanol (satisfying GB338-2004 first class) from outside the reactor and air are fed into methanol oxidation stage 13 via pipelines 11 and 12, respectively, at the top of the reactor, and are reacted, for example, at a temperature ranging from 200° C. to 228° C. to produce a gas mixture comprising polyoxymethylene dimethyl ethers. The produced gas mixture is quenched down to a temperature of 100-120° C. in the quenching stage of the reactor to inhibit, for example, to prevent, the reaction product from being thermally degraded or to inhibit, for example, to prevent, an intermediate product formaldehyde from being polymerized into polyformaldehydes. The cooled reaction product 14 is fed into product separation stage 15 and a part of the methanol may be fed into product separation stage 15 as an absorbing liquid. In the product separation stage, polyoxymethylene dimethyl ethers are absorbed by a cycled liquid flowing from the top to the bottom of the column, and the remaining tail gas containing trace amounts of polyoxymethylene dimethyl ethers and formaldehyde are passed to a tail gas processor (stage not shown) and burned. Methanol, dimethyl ether, formaldehyde, methylal, and water in the product comprising polyoxymethylene dimethyl ethers are vaporized in the product separation stage. Dimethyl ether from the separation stage can be recycled back to the oxidation stage and used as an inert medium. During the product separation stage, distillation ranges and flash points of the desired products can be controlled so that a polyoxymethylene dimethyl ethers product 16 having diesel oil-like properties can be obtained.

According to the representative procedure shown by FIG. 1, methanol and an oxidant are fed into the methanol conversion reaction stage 13 via 11 and 12, respectively. The reaction products of the conversion reaction are fed into separation stage 15 via 14 to obtain dimethyl ether, formaldehyde, methylal, water, and polyoxymethylene dimethyl ethers. The products are removed via 16. The reaction stage 13 comprises a quenching exchanger, in which the reaction product is quenched to a temperature to be lower than the temperature at which polyoxymethylene dimethyl ethers may be degraded, or lower than the temperature at which intermediate product formaldehyde may be polymerized into polyformaldehyde, such as 100-120° C., so as to inhibit, such as to prevent, polyoxymethylene dimethyl ethers from being thermally degraded, or to inhibit, such as to prevent, intermediate product formaldehyde from being polymerized into polyformaldehyde. Then the reaction product is fed into product separation stage 15 via 14.

Figure 2:
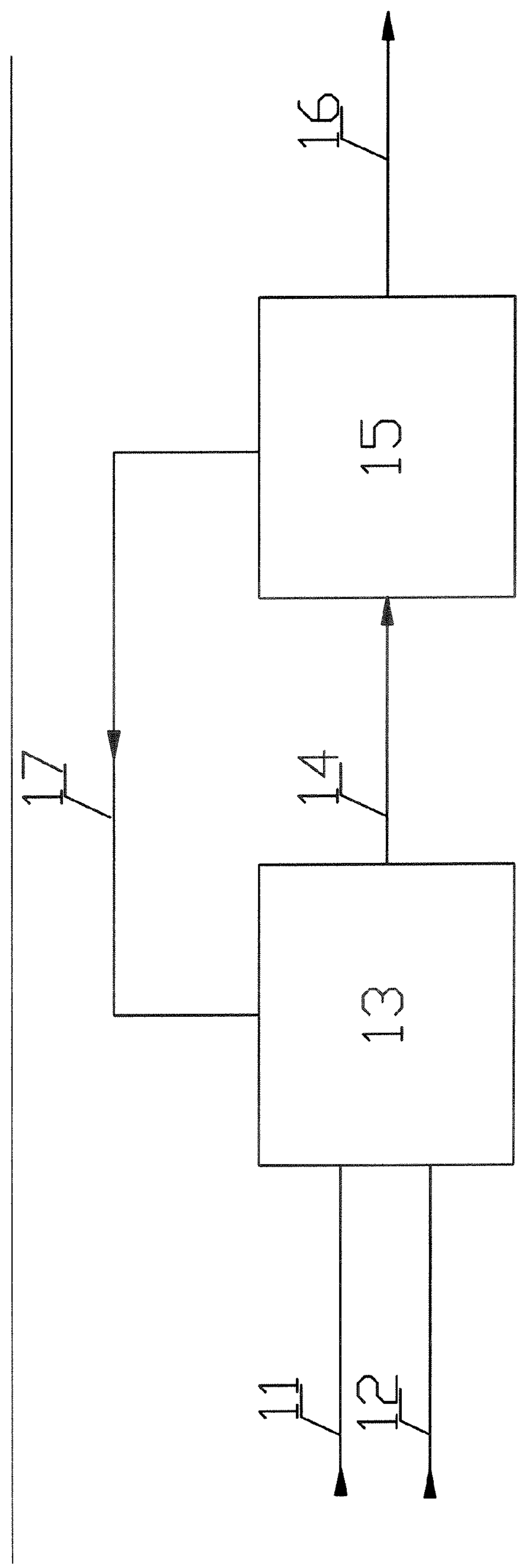
FIG. 2 is a representative schematic view of a process of preparing polyoxymethylene dimethyl ethers from methanol in one step according to another embodiment disclosed herein.

Another representative embodiment disclosed herein is conducted according to the procedure shown in FIG. 2. As shown in FIG. 2, a stage 17 for cycling at least a portion of non-DMMx parts in the reaction product to reaction stage 13 is added, with everything else being the same as in FIG. 1.

The embodiments of the present disclosure described herein are representative and not limitative. Disclosed embodiments herein of the invention include the following non-limitative examples. Examples 1-7 illustrate catalysts, which can be used in the process disclosed herein, and the method of preparing the same.

EXAMPLE 1

51 g of ammonium molybdate and 5 g of ferric nitrate were dissolved in 3 L de-ionized water to form a solution, followed by adding to the solution 700 g of a M-5 molecular sieve (a $SiO_2/Al_2O_3$ (in moles) of 50, available from Changling Catalyst Plant). After 5 hours, the mixture was filtered and dried at 200° C. for 2 hours, and calcinated at 500° C. for 1 hour, resulting in catalyst C1 (here and hereafter, "C1" refers to the catalyst obtained in Example 1). The components of the catalyst C1 are reported in Table 1.

EXAMPLE 2

51 g of ammonium molybdate and 5 g of ferric nitrate were dissolved in 3 L de-ionized water to form a solution, followed by adding to the solution 700 g of a USY molecular sieve (available from Changling Catalyst Plant). After 5 hours, the mixture was filtered and dried at 200° C. for 2 hours, and calcinated at 500° C. for 1 hour, resulting in catalyst C2. The components of the catalyst C2 are reported in Table 1.

EXAMPLE 3

51 g of ammonium molybdate and 5 g of ferric nitrate were dissolved in 3 L de-ionized water to form a solution, followed by adding to the solution 700 g of a REY molecular sieve (a rare earth content of 6 wt %, available from Changling Catalyst Plant). After 5 hours, the mixture was filtered and dried at 200° C. for 2 hours, and calcinated at 500° C. for 1 hour, resulting in catalyst C3. The components of the catalyst C3 are reported in Table 1.

EXAMPLE 4

80 g of ammonium molybdate and 4 g of ferric nitrate were dissolved in 3 L de-ionized water to form a solution, followed by adding to the solution 700 g of a REY molecular sieve (a rare earth content of 6 wt %, available from Changling Catalyst Plant). After 5 hours, the mixture was filtered and dried at 200° C. for 2 hours, and calcinated at 500° C. for 1 hour, resulting in catalyst C4. The components of the catalyst C4 are reported in Table 1.

EXAMPLE 5

51 g of ammonium molybdate and 5 g of ferric nitrate were dissolved in 3 L de-ionized water to form a solution, followed by adding to the solution 700 g of a REY molecular sieve (a rare earth content of 6 wt %, available from Changling Catalyst Plant) while stirring at 30° C. for 5 hours. Then the catalyst was placed in an oven at 200° C. for 2 hours, resulting in catalyst C5. The components of the catalyst C5 are reported in Table 1.

EXAMPLE 6

51 g of ammonium molybdate and 5 g of ferric nitrate were dissolved in 3 L de-ionized water to form a solution, followed by adding to the solution 700 g of a HY molecular sieve (available from Changling Catalyst Plant). After 5 hours, the mixture was filtered and dried at 200° C. for 2 hours, and calcinated at 500° C. for 1 hour, resulting in catalyst C6. The components of the catalyst C6 are reported in Table 1.

EXAMPLE 7

700 g of a REY molecular sieve (a rare earth content of 6 wt %, available from Changling Catalyst Plant) and 10 wt % of $Al_2O_3$ (based on the molecular sieve) were mixed and extrusion-molded into strips by a columned orifice-plate having a diameter of 1.2 mm. The wet strips were dried at 120° C. for 3 hours, and calcinated at 500° C. for 2 hours, resulting in a catalyst carrier. When the temperature of the carrier was dropped to room temperature, it was impregnated with 3 L aqueous solution containing 51 g of ammonium molybdate and 5 g of ferric nitrate for 5 hours. Then, the carrier was filtered and dried at 200° C. for 2 hours, and calcinated at 500° C. for 1 hour to obtain catalyst C7. The components of the catalyst C7 are reported in Table 1.

EXAMPLE 8

700 g of a REY molecular sieve (a rare earth content of 6 wt %) and 30 wt % of $SiO_2$—$Al_2O_3$ (based on the molecular sieve) were mixed to form a mixture of molecular sieve and $SiO_2$—$Al_2O_3$. 51 g of ammonium molybdate and 5 g of ferric nitrate were dissolved in 3 L de-ionized water to form a solution, into which the mixture of the molecular sieve and $SiO_2$—$Al_2O_3$ were added. After 5 hours, the mixture was filtered and dried at 200° C. for 2 hours, and calcinated at 500° C. for 1 hour to obtain catalyst C8. The components of the catalyst C8 are reported in Table 1.

EXAMPLE 9

102 g of ammonium molybdate and 10 g of ferric nitrate were dissolved in 3 L de-ionized water to form a solution, followed by adding to the solution 700 g of a REY molecular sieve (a rare earth content of 6 wt %, available from Changling Catalyst Plant). The mixture was stirred at 30° C. for 5 hours. Then the catalyst was placed in an oven at 200° C. for 2 hours to obtain catalyst C9. The components of the catalyst C9 are reported in Table 1.

TABLE 1

| Example | Catalyst | Molecular Sieve, % | Matrix, % | Molybdenum oxide, % | Ion oxide, % |
|---|---|---|---|---|---|
| 1 | C1 | 86.48 | 0 | 8.40 | 5.12 |
| 2 | C2 | 90.18 | 0 | 8.36 | 1.46 |
| 3 | C3 | 90.71 | 0 | 8.67 | 0.62 |
| 4 | C4 | 87.57 | 0 | 11.96 | 0.47 |
| 5 | C5 | 91.83 | 0 | 7.61 | 0.56 |
| 6 | C6 | 95.08 | 0 | 4.57 | 0.35 |
| 7 | C7 | 83.60 | 8.36 | 7.62 | 0.42 |
| 8 | C8 | 71.16 | 21.35 | 7.12 | 0.37 |
| 9 | C9 | 75.42 | 0 | 17.06 | 7.52 |

EXAMPLE 10

According to the procedure shown by FIG. 2, a conversion of methanol was conducted, wherein the feed of methanol was first class methanol under GB338-2004, the reactor was a shell and tube fixed reactor, the cooling medium was water, and the catalyst was C5.

The feed amount of methanol was 12000 kg/h, the conversion rate of methanol in one run was more than 96-98%, the output amount of DMMx was 4080 kg/h and the cycling dimethyl ether was in an amount of 10000 kg/h. The other reaction conditions were listed in Table 2, and the reaction products were listed in Table 3. The result shows the selectivity of DMMx may be up to 33% under the above operating conditions.

TABLE 2

| reactor conditions<br>reaction conditions | |
|---|---|
| Temperature | 250° C. |
| Pressure | 1.0 MPa(G) |
| Oxygen/methanol | 0.3 |
| Conversion rate of methanol in one run | 98 |
| Selectivity of DMMx | 33 |
| Weight space velocity ($h^{-1}$) | 12 |

TABLE 3

| the composition of the products fed into the absorbing system<br>Composition of products | |
|---|---|
| DMMx | 34% |
| Methanol | 2% |
| formaldehyde | 3% |
| methylal | 3% |
| Water | 5% |
| Dimethyl ether | 23% |
| Carbon monooxide | 8% |
| Carbon dioxide | 22% |

Examples 11-24 illustrate the process disclosed herein and the results thereof. The reactions took place in a fixed-bed reactor. The methanol was an analytical reagent available from Beijing Chemical Works, and the oxidant was air. Catalysts C1-C6 and C9 were pressed into tablets, broken and sieved, resulting in particles of 20-40 meshes. Catalysts C7-C8 were broken and sieved, resulting in particles of 20-40 meshes.

Table 4 summarizes the catalyst used in each example and reaction conditions. Two hours after the reactions, samples were taken out for analysis using Agilent 6890 Chromatography.

$$\text{Methanol conversion}=((MOH_{before\ reaction}-MOH_{after\ reaction})/MOH_{before\ reaction})\times 100\%$$

$$\text{Selectivity of polyoxymethylene dimethyl ether}=(DMM_X/(MOH_{before\ reaction}-MOH_{after\ reaction}))\times 100\%$$

The results are reported in Table 5.

TABLE 4

| Example | Catalyst | Temperature, ° C. | Pressure, MPa | Space Velocity, $h^{-1}$ | Oxygen/ Methanol |
|---|---|---|---|---|---|
| 11 | C1 | 250 | 0.3 | 13 | 0.30 |
| 12 | C2 | 150 | 0.3 | 10 | 0.15 |
| 13 | C2 | 250 | 0.4 | 13 | 0.20 |
| 14 | C3 | 250 | 1.1 | 13 | 0.20 |
| 15 | C3 | 250 | 0.3 | 13 | 0.25 |
| 16 | C4 | 250 | 0.5 | 13 | 0.20 |
| 17 | C5 | 250 | 0.4 | 13 | 0.20 |
| 18 | C5 | 250 | 1.6 | 13 | 0.30 |
| 19 | C6 | 350 | 0.3 | 20 | 0.10 |
| 20 | C6 | 250 | 0.2 | 13 | 0.20 |
| 21 | C7 | 250 | 1.6 | 13 | 0.10 |
| 22 | C8 | 300 | 1.1 | 13 | 0.10 |
| 23 | C9 | 250 | 1.1 | 13 | 0.20 |
| 24 | C9 | 250 | 0.3 | 13 | 0.20 |

TABLE 5

| Example | Catalyst | Methanol Conversion/% | DMMx Selectivity/% |
|---|---|---|---|
| 11 | C1 | 83.4 | 7.1 |
| 12 | C2 | 81.4 | 15.9 |
| 13 | C2 | 82.9 | 16.2 |
| 14 | C3 | 97.2 | 26.4 |
| 15 | C3 | 96.0 | 26.1 |
| 16 | C4 | 97.6 | 31.7 |
| 17 | C5 | 97.1 | 26.6 |
| 18 | C5 | 98.4 | 34.1 |
| 19 | C6 | 87.1 | 10.9 |
| 20 | C6 | 84.9 | 11.7 |
| 21 | C7 | 94.1 | 21.4 |
| 22 | C8 | 89.2 | 17.2 |
| 23 | C9 | 97.4 | 27.9 |
| 24 | C9 | 93.5 | 24.2 |

Processes disclosed herein, such as that in Example 18, can convert methanol directly to dimethyl ether and polyoxymethylene dimethyl ether ($DMM_X$, $2\leqq x\leqq 8$) in one step. In Example 18, the methanol conversion can reach 98.4% and DMMx selectivity can reach 34.1% when using a REY molecular sieve in the catalyst. The process disclosed herein can be suitable in circumstances requiring a high yield of DMMx.

We claim:

1. A process for preparing polyoxymethylene dimethyl ether from methanol, comprising contacting methanol with at least one oxidant in the presence of at least one catalyst, wherein the at least one catalyst comprises at least one Group VIB metal component, at least one Group VIII metal component, and at least one molecular sieve having acidic catalytic activity for a time sufficient to obtain polyoxymethylene dimethyl ether, wherein the metal components in the at least one catalyst are chosen from a group consisting of Group VIB metal components and Group VIII metal components, and wherein the at least one Group VIB metal component and the at least one Group VIII metal component are independently chosen from oxides, salts, and sulfides.

2. The process of claim 1, wherein said at least one Group VIB metal component is present in the at least one catalyst in an amount of from about 0.5 to about 50 wt % (in terms of metal oxide), said at least one Group VIII metal component is present in an amount of from about 0.2 to about 20 wt % (in terms of metal oxide), and said at least one molecular sieve having acidic catalytic activity is present in an amount of from about 40 to about 95 wt %, based on the total weight of the at least one catalyst.

3. The process of claim 1, wherein the at least one Group VIB metal component comprises molybdenum, and wherein the at least one Group VIII metal component comprises iron.

4. The process of claim 3, wherein the amount of the at least one Group VIB metal component, in terms of metal oxide, ranges from about 2 to about 20 wt % and the amount of the at least one Group VIII metal component, in terms of metal oxide, ranges from about 0.2 to about 10 wt % based on the total weight of the at least one catalyst.

5. The process of claim 1, wherein the at least one molecular sieve having acidic catalytic activity is chosen from mesoporous molecular sieves and macroporous molecular sieves.

6. The process of claim 5, wherein the amount of the at least one molecular sieve ranges from about 70 to about 90 wt % based on the total weight of the at least one catalyst.

7. The process of claim 5, wherein the mesoporous molecular sieves are chosen from at least one ZSM-5 molecular sieves, and the macroporous molecular sieves are chosen from at least one Y-type molecular sieves.

8. The process of claim 7, wherein the Y-type molecular sieves are chosen from HY, REY, REHY, USY, and REUSY.

9. The process of claim 8, wherein the Y-type molecular sieves are chosen from REY and REHY.

10. The process of claim 1, wherein the at least one catalyst further comprises at least one heat-resistant inorganic oxide matrix.

11. The process of claim 10, wherein said at least one heat-resistant inorganic oxide matrix is present in an amount of no more than 80 wt %, based on the total weight of the at least one catalyst.

12. The process of claim 10, wherein the at least one heat-resistant inorganic oxide matrix is chosen from alumina, silica, and silica-alumina.

13. The process of claim 12, wherein the at least one heat-resistant inorganic oxide matrix is present in an amount of no more than 60 wt %, based on the total weight of the at least one catalyst.

14. The process of claim 1, wherein conditions for said contacting for said time sufficient comprise a temperature ranging from about 50° C. to about 500° C., a pressure ranging from about 0.1 MPa to about 10 MPa, and a mass space velocity of methanol feed ranging from about 0.5 $h^{-1}$ to about 50 $h^{-1}$, and further wherein the content of the at least one oxidant is selected such that the molar ratio of oxygen in said at least one oxidant to methanol in said contacting for said time sufficient ranges from about 0.01:1 to about 0.5:1.

15. The process of claim 14, wherein the conditions for said contacting for said time sufficient comprise a temperature ranging from about 100° C. to about 400° C., a pressure ranging from about 0.1 MPa to about 5 MPa, and a mass space velocity of said methanol feed ranging from about 3 to about 30 $h^{-1}$, and further wherein the content of the oxidant is selected so that the molar ratio of oxygen in said at least one oxidant to methanol in said contacting for said time sufficient ranges from about 0.05:1 to about 0.3:1.

16. The process of claim 15, wherein the conditions for said contacting for said time sufficient comprise a temperature ranging from about 100° C. to about 300° C., a pressure ranging from about 0.1 MPa to about 2 MPa, and a mass space velocity of said methanol feed ranging from about 8 to about 20 $h^{-1}$.

17. The process of claim 1, wherein the at least one oxidant is chosen from oxygen, air, and a gas mixture of air and/or oxygen with at least one additional gas, which is inert to methanol.

18. The process of claim 17, wherein said at least one additional gas is chosen from nitrogen and other gases inert to methanol.

19. The process of claim 17, wherein the amount of oxygen in the gas mixture ranges from about 1 to about 30% by volume of the gas mixture.

20. A gas-phase process of preparing polyoxymethylene dimethyl ethers (DMMx) from methanol, comprising mixing methanol and at least one oxidant to form a binary mixed gas of said methanol and said at least one oxidant, feeding the mixed gas into a reactor, and passing the mixed gas through a catalyst bed to form a product mixture containing DMMx, and adjusting the temperature of the reactor under controlled thermal conditions, wherein the catalyst bed comprises at least one catalyst, wherein the at least one catalyst comprises at least one Group VIB metal component, at least one Group VIII metal component, and at least one molecular sieve having acidic catalytic activity for a time sufficient to obtain polyoxymethylene dimethyl ether, wherein the metal components in the at least one catalyst are chosen from a group consisting of Group VIB metal components and Group VIII metal components, and wherein the at least one Group VIB metal component and the at least one Group VIII metal component are independently chosen from oxides, salts, and sulfides.

21. The process of claim 20, wherein said adjusting the temperature of the reactor under controlled thermal conditions comprise controlling a cycled amount of non-DMMx parts in the product mixture to adjust the temperature of the reactor.

22. The process of claim 21, wherein said controlling the cycled amount of the non-DMMx parts in the product mixture comprises incorporating said non-DMMx parts in the product mixture into said catalyst bed directly from the top of the reactor or from multi-points at separate stages, and controlling the temperature of the cycled non-DMMx parts at a temperature of from about 0° C. to about 150° C.

23. The process of claim 21, wherein the ratio of the amount of the cycled non-DMMx parts to the starting amount of the methanol is from about 0.1:1 to about 100:1.

24. The process of claim 20, wherein said adjusting the temperature of the reactor under controlled thermal conditions comprises cooling with at least one cooling medium outside the catalyst bed.

25. The process of claim 24, wherein the at least one cooling medium is chosen from air, water, and heat transfer oil.

26. The process of claim 20, further comprising feeding the product mixture containing DMMx into a separation stage.

27. The process of claim 20, wherein the catalyst bed is a fixed bed, and the at least one catalyst in said catalyst bed comprises at least one Group VIB metal component, at least one Group VIII metal component, and at least one molecular sieve having acidic catalytic activity.

28. The process of claim 20, wherein the at least one oxidant is chosen from oxygen, air, and a gas mixture of air and/or oxygen with at least one additional gas which is inert to said methanol.

29. The process of claim 20, wherein conditions for said process comprise a temperature ranging from about 50° C. to about 500° C., a pressure ranging from about 0.1 MPa to about 10 MPa, and a mass space velocity of methanol feed ranging from about 0.5 $h^{-1}$ to about 50 $h^{-1}$, and further wherein the at least one oxidant is present in an amount such that the molar ratio of oxygen in said at least one oxidant to the starting amount of said methanol ranges from about 0.01:1 to about 0.5:1.

30. The process of claim 29, wherein said conditions comprise a temperature ranging from about 100 to about 400° C., a pressure ranging from about 0.1 MPa to about 5 MPa, a mass space velocity of said methanol feed ranging from about 3 to about 30 $h^{-1}$, and further wherein said at least one oxidant is selected in an amount such that the molar ratio of oxygen in said at least one oxidant to the starting amount of said methanol ranges from about 0.05:1 to about 0.3:1.

31. The process of claim 30, wherein said conditions comprise a temperature ranging from about 100 to about 300° C., a pressure ranging from about 0.1 MPa to about 2 MPa, and a mass space velocity of said methanol feed of about 8 to about 20 $h^{-1}$.

* * * * *